United States Patent
Köhler et al.

(10) Patent No.: US 7,253,252 B2
(45) Date of Patent: Aug. 7, 2007

(54) WATER-SOLUBLE ASPARTATE

(75) Inventors: Burkhard Köhler, Leverkusen (DE); Meike Niesten, Köln (DE); Joachim Simon, Düsseldorf (DE); Christian Wamprecht, Neuss (DE)

(73) Assignee: Bayer MaterialScience AG, Leverkusen (DE)

( * ) Notice: Subject to any disclaimer, the term of this patent is extended or adjusted under 35 U.S.C. 154(b) by 35 days.

(21) Appl. No.: 11/178,708

(22) Filed: Jul. 11, 2005

(65) Prior Publication Data
US 2006/0014922 A1 Jan. 19, 2006

(30) Foreign Application Priority Data
Jul. 15, 2004 (DE) .................. 10 2004 034 271

(51) Int. Cl.
*C08G 69/10* (2006.01)

(52) U.S. Cl. .................. 528/328; 510/434; 528/44; 528/59; 528/61; 528/310

(58) Field of Classification Search ................. 510/434; 528/44, 59, 61, 310, 328
See application file for complete search history.

(56) References Cited

U.S. PATENT DOCUMENTS

| 5,075,370 | A | | 12/1991 | Kubitza et al. ............. 524/591 |
| 5,126,170 | A | | 6/1992 | Zwiener et al. .......... 427/385.5 |
| 5,236,741 | A | | 8/1993 | Zwiener et al. .......... 427/385.5 |
| 5,714,632 | A | * | 2/1998 | Rao et al. .................. 562/450 |
| 5,736,604 | A | * | 4/1998 | Luthra ........................ 524/591 |
| 5,925,711 | A | | 7/1999 | Wamprecht et al. ........ 524/539 |

\* cited by examiner

*Primary Examiner*—Terressa Boykin
(74) *Attorney, Agent, or Firm*—Joseph C. Gil; Lyndanne M. Whalen

(57) ABSTRACT

The present invention relates to new water-soluble polyaspartic esters and also to their use in aqueous coating compositions.

11 Claims, No Drawings

WATER-SOLUBLE ASPARTATE

CROSS REFERENCE TO RELATED APPLICATION

This application claims priority under 35 U.S.C. §119 to German patent application DE 10 2004 034 271.7, filed Jul. 15, 2004.

FIELD OF THE INVENTION

The present invention relates to new water-soluble polyaspartic esters and also to their use as aqueous coating compositions.

BACKGROUND OF THE INVENTION

Two-component coating compositions comprising a polyisocyanate component binder in combination with a reactive component that is reactive toward isocyanate groups, in particular a polyhydroxyl component, have long been known. They are suitable for producing high-grade coatings, which can be made hard, elastic, abrasion-resistant and solvent-resistant.

In view of the fact that primary amines undergo a spontaneous and rapidly uncontrollable reaction with polyisocyanates they are unsuitable as reaction partners for polyisocyanates in two-component coatings.

EP-A 0 403 921 describes low-viscosity polyaspartic esters which contain secondary amino groups and whose reactivity towards NCO groups is therefore moderate as compared with primary amines. Polyaspartic esters of this kind are particularly suitable for preparing low-solvent or solvent-free coating compositions which exhibit rapid curing.

Polyaspartic esters of this kind are, however, not water-soluble or water-dispersible, and so are not suitable for use in aqueous binders.

In view of the evermore stringent legislation governing permitted levels of volatile organic components in, for example, coating compositions, there is increasing demand for aqueous systems. Aqueous two-component coating compositions have been known for years and are described for example in EP-A 0 358 979.

EP-B 0 818 492 describes aqueous secondary polyamines which are obtained by Michael Addition of polyamines with oligoesters containing maleic ester units. A disadvantage of such products is that reaction of the polyisocyanate may be followed by the formation of hydantoin, as a result of which the oligoester chains are cleaved. This in turn leads to a loss of mechanical properties on the part of the coating.

EP-A 0 849 301 describes aqueous binder mixtures based on polyaspartic esters and aqueous polyisocyanates. A disadvantage, however, is that these polyaspartic esters are not water-dispersible or water-soluble, and so cannot be provided in the form of storage-stable aqueous formulations. The coatings must therefore be produced by adding the aqueous polyisocyanate to the hydrophobic polyaspartic ester, then mixing the system with water and applying it immediately.

For reasons of improved processing, however, it would be desirable to be able to use water-soluble or water-dispersible aspartates or aqueous formulations thereof in such systems.

SUMMARY OF THE INVENTION

An object of this invention was therefore to provide water-soluble polyaspartic esters for preparing aqueous two-component (2K) coating compositions for producing polyurea coatings and/or polyurea-polyurethane coatings.

It has now been found that water-soluble polyaspartic esters can be prepared by reacting amines with maleic esters containing one or more ethylene oxide units. The invention accordingly provides hydrophilic polyaspartic esters of the general formula (I), (I)

where
R is a $C_1$-$C_4$ alkyl radical,
A and A' independently of one another are hydrogen or methyl,
X is an n-valent aliphatic, araliphatic or cycloaliphatic radical having 1 to 20 carbon atoms and optionally containing ether bridges,
l and m are natural numbers from 0 to 10 whose sum l+m=1 to 20, and
n is a natural number from 1 to 3.

The invention further provides a process for preparing the polyaspartic esters of the invention, in which maleic esters of the general formula (II), (II)

are reacted with an n-valent amine of the formula (III), (III)

at temperatures of 0 to 100° C., preferably of 15 to 50° C., preferably without solvent.

The meaning of n, X, R, A, A', l and m corresponds to the definitions indicated above for formula (I).

The invention accordingly further provides aqueous solutions or dispersions comprising the polyaspartic esters of the invention.

Likewise provided for the present invention are two-component (2K) coating compositions for preparing polyurethane-polyurea coatings, comprising at least one hydro-

DETAILED DESCRIPTION OF THE INVENTION

The invention accordingly provides hydrophilic polyaspartic esters of the general formula (I),

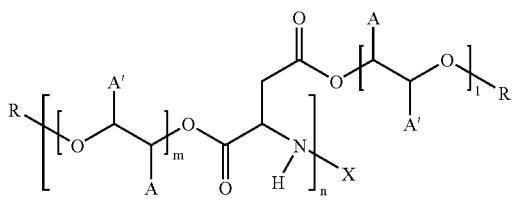

where

R is a $C_1$-$C_4$ alkyl radical,

A and A' in dependently of one another are hydrogen or methyl,

X is an n-valent aliphatic, araliphatic or cycloaliphatic radical having 1 to 20 carbon atoms and optionally containing ether bridges, l and m are natural numbers from 0 to 10 whose sum l+m=1 to 20, and n is a natural number from 1 to 3.

Preferably A and A' are hydrogen.

Preferably X is an n-valent aliphatic or cycloaliphatic radical having 1 to 10 carbon atoms and optionally containing ether bridges.

Preferably l and m independently of one another are natural numbers from 1 to 3. Preferably the sum of l+m=2 to 6.

Typically the polyaspartic esters of the invention have number-average molecular weights of 300 g/mol to 1000 g/mol, preferably 400 g/mol to 750 g/mol.

Typically the polyaspartic esters of the invention have viscosities (measured with a rotational viscometer) at 23° C. of 50 to 5000 mPas, preferably 50 to 2500 mPa·s. With particular advantage the polyaspartic esters of the invention are soluble in water even without neutralization (complete or partial protonation of the amino functions present).

The invention further provides a process for preparing the polyaspartic esters of the invention, in which maleic esters of the general formula (II),

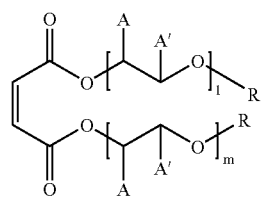

are reacted with an n-valent amine of the formula (III),

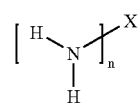

at temperatures of 0 to 100° C., preferably of 15 to 50° C., preferably without solvent.

The meaning of n, X, R, A, A', l and m corresponds to the definitions indicated above for formula (I).

Amines of the formula (II) used with particular preference are 1,2-ethylenediamine, 1,2-diaminopropane, 1,4-diaminobutane, 1,6-diaminohexane, 2,5-diamino-2,5-dimethylhexane, 2,2,4- and/or 2,4,4-trimethyl-1,6-diaminohexane, 1,11-diaminoundecane, 1,12-diaminododecane, 4-aminoethyl-1,8-diaminooctane, 1-amino-3,3,5-trimethyl-5-aminomethylcyclohexane, 2,4- and/or 2,6-hexahydrotolylenediamine, 2,4'- and/or 4,4'-diaminodicyclohexylmethane, 3,3'-dimethyl-4,4'-diaminodicyclohexylmethane, 2,4,4'-triamino-5-methyldicyclohexylmethane and polyether polyamines having aliphatically attached primary amino groups and a number-average molecular weight $M_n$ of 148 to 6000 g/mol is obtained.

The maleic esters of the formula (II) are obtainable by complete or partial transesterification of maleic esters with monohydroxy-functional ethers.

Preferred maleic esters used are dimethyl maleate, diethyl maleate, dipropyl maleate, diisopropyl maleate, dibutyl maleate, di-tert-butyl maleate, di-sec-butyl maleate or diisobutyl maleate. Particular preference is given to dimethyl maleate or diethyl maleate, very particular preference to dimethyl maleate.

The monohydroxy-functional ethers correspond to the formula (IV),

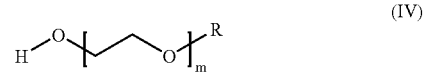

where

R and m have the definition laid down in connection with formula (I).

Ethers of the formula (IV) used are preferably ethylene glycol monomethyl ether, diethylene glycol monomethyl ether or triethylene glycol monomethyl ether.

The reactants are reacted typically in a molar ratio of 1:10 to 4:1 (maleic ester to alcohol of the formula (IV)) at temperatures of 100 to 200° C., preferably of 120 to 160° C. in the presence of catalysts.

Catalysts used are typically compounds based on tin, titanium, alkali metals or alkaline earth metals. Preferred catalysts are tin-based compounds such as dibutyltin oxide or dibutyltin dilaurate, for example.

In order to shift the equilibrium the alcohol liberated during the transesterification is preferably removed by distillation. The progress of the reaction can be monitored on the basis of the amount of alcohol removed by distillation. The reaction is typically continued until the theoretically calculated amount of alcohol has been distilled off.

In the case where the ether of the formula (IV) has been used in excess amount relative to the sum of the ester functions present, it too may be distilled off after the end of the transesterification.

The resultant maleic esters of the formula (II) are then used, preferably without a further purification step, in the reaction to give the polyaspartic ester. Distillative purification can take place in principle, but should be carried out only in the case of those products which have molar weights of below 300 g/mol, since otherwise distillation may be accompanied by product decomposition.

Another way of preparing the maleic esters of the formula (II) is to react maleic anhydride with ethers of the formula (IV), operating at temperatures of 80 to 160° C. and removing the water of reaction by means of suitable distillation techniques. Additionally use is made as well of acidic catalysts such as sulphuric acid, p-toluenesulphonic acid or acidic ion exchangers.

This way is employed in particular when ethylene glycol monoalkyl ether is used for ether of the formula (IV).

The hydrophilic polyaspartic esters of the invention can be resolved without problems in water or formulated without problems as stable dispersions. For this purpose it is commonly enough to mix the ester with water, although the use, if desired, of mechanical assistants such as high-speed stirrers or dispersers is also possible.

Such dispersions or solutions typically have concentrations, based on the polyaspartic ester, of 30% to 95% by weight, preferably 50% to 90% by weight.

The invention accordingly further provides aqueous solutions or dispersions comprising the polyaspartic esters of the invention.

Likewise provided for the present invention are two-component (2K) coating compositions for preparing polyurethane-polyurea coatings, comprising
  a) at least one hydrophilic polyaspartic ester of the formula (I) according to the invention,
  b) water,
  c) at least one polyisocyanate and
  d) optionally auxiliaries and additives.

The NCO:NH equivalent ratio is typically 0.5:1 to 3.0:1, preferably 0.8:1 to 2.5:1.

Suitable polyisocyanates of component c) are organic polyisocyanates having an average NCO functionality of at least 2 and a molecular weight of at least 140 g/mol. Of particularly high suitability are (i) unmodified organic polyisocyanates of the number-average molecular weight range from 140 to 300 g/mol, (ii) paint polyisocyanates with a number-average molecular weight of 300 to 1000 g/mol, and (iii) NCO prepolymers containing urethane groups and having number-average molecular weights>1000 g/mol, or mixtures of (i) to (iii).

Examples of polyisocyanates of group (i) are 1,4-diisocyanatobutane, 1,6-diisocyanatohexane (HDI), 1,5-diisocyanato-2,2-dimethylpentane, 2,2,4- and 2,4,4-trimethyl-1,6-diisocyanatohexane, 1-isocyanato-3,3,5-trimethyl-5-isocyanatomethylcyclohexane (IPDI), 1-isocyanato-1-methyl-4(3)-isocyanatomethylcyclohexane, bis(4-isocyanatocyclohexyl)methane, 1,10-diisocyanatodecane, 1,12-diisocyanatododecane, cyclohexane 1,3- and 1,4-diisocyanate, xylylene diisocyanate isomers, triisocyanatononane (TIN), 2,4-diisocyanatotoluene or its mixtures with 2,6-diisocyanatotoluene with, preferably, based on mixtures, up to 35% by weight 2,6-diisocyanatotoluene, 2,2'-, 2,4'-, 4,4'-diisocyanatodiphenylmethane or technical polyisocyanate mixtures of the diphenylmethane series or any desired mixtures of the isocyanates mentioned.

Polyisocyanates of group (ii) are the paint polyisocyanates that are known per se. The term "paint polyisocyanates" comprehends, for the purposes of the invention, compounds or mixtures of compounds which are obtained by conventional oligomerization reaction of simple diisocyanates of the type exemplified under (i).

Examples of suitable oligomerization reactions are carbodiimidization, dimerization, trimerization, biuretization, urea formation, urethanization, allophanatization and/or cyclization with the formation of oxadiazine structures. Often in the course of "oligomerization" two or more of the said reactions proceed simultaneously or in succession.

Preferably the "paint polyisocyanates" (ii) comprise biuret polyisocyanates, polyisocyanates containing isocyanurate groups, polyisocyanate mixtures containing isocyanurate groups and uretdione groups, polyisocyanates containing urethane and/or allophanate groups, or polyisocyanate mixtures containing isocyanurate and allophanate groups, said polyisocyanate mixtures being based on simple diisocyanates.

The preparation of such paint polyisocyanates is known and is described for example in DE-A 1 595 273, DE-A 3 700 209 and DE-A 3 900 053 or in EP-A-0 330 966, EP-A 0 259 233, EP-A-0 377 177, EP-A-0 496 208, EP-A-0 524 501 or U.S. Pat. No. 4,385,171.

Polyisocyanates of group (iii) are the prepolymers that are known per se and contain isocyanate groups and are based on simple diisocyanates of the type exemplified above and/or are based on paint polyisocyanates (ii) on the one hand and organic polyhydroxy compounds having a number-average molecular weight of more than 300 g/mol on the other. While the paint polyisocyanates of group (ii) that contain urethane groups are derivatives of low molecular weight polyols, of the number-average molecular weight range from 62 to 300 g/mol, examples of suitable polyols being ethylene glycol, propylene glycol, trimethylolpropane, glycerol or mixtures of these alcohols, the polyhydroxyl compounds used for preparing the NCO prepolymers of group (iii) have number-average molecular weights of more than 300 g/mol, preferably more than 500 g/mol, more preferably from 500 to 8000 g/mol. Polyhydroxyl compounds of this kind are in particular those which contain per molecule 2 to 6, preferably 2 to 3, hydroxyl groups and are selected from the group consisting of ether, ester, thioether, carbonate and polyacrylate polyols and mixtures of such polyols.

In connection with the preparation of the NCO prepolymers (iii) the stated higher molecular weight polyols can also be employed in blends with the stated low molecular mass polyols, so as to result directly in mixtures of low molecular mass paint polyisocyanates (ii) containing urethane groups and higher molecular weight NCO prepolymers (iii), which are likewise suitable as a starting component (C) according to the invention.

For preparing the NCO prepolymers (iii) or their mixtures with the paint polyisocyanates (ii), diisocyanates (i) of the type exemplified above or paint polyisocyanates of the type exemplified under (ii) are reacted with the higher molecular weight hydroxyl compounds or their mixtures with low molecular weight polyhydroxyl compounds of the type exemplified, observing an NCO/OH equivalent ratio of 1.1:1 to 40:1, preferably 2:1 to 25:1, with the formation of urethane. Optionally it is possible, when using an excess of distillable starting diisocyanate, to remove it by distillation following the reaction, so that monomer-free NCO prepolymers, i.e. mixtures of starting diisocyanates (i) and true NCO prepolymers (iii), are present and may likewise be used as component (A).

Low-viscosity, hydrophilicized polyisocyanates having free isocyanate groups and based on aliphatic, cycloaliphatic, araliphatic and/or aromatic isocyanates, more preferably aliphatic or cycloaliphatic isocyanates, can also be employed.

Hydrophilicization of the polyisocyanates is possible, for example, by reaction with substoichiometric amounts of monofunctional, hydrophilic polyether alcohols. The preparation of hydrophilicized polyisocyanates of this kind is described for example in EP-A 0 540 985, p. 3, l. 55-p. 4, l. 5. Also highly suitable are the polyisocyanates containing allophanate groups that are described in EP-A-959087, p. 3, l. 39-51 and are prepared by reacting polyisocyanates of low monomer content with polyethylene oxide polyether alcohols under allophanatization conditions. Also suitable are the water-dispersible polyisocyanate mixtures based on triisocyanatononane that are described in DE-A 100 078 21, p. 2, l. 66-p. 3, l. 5, and also polyisocyanates hydrophilicized with ionic groups (sulphonate groups, phosphonate groups), as described for example in DE 10024624, p. 3, l. 13-33. A further possibility is that of hydrophilicization by addition of commercially customary emulsifiers.

Also possible in principle, of course, is the use of mixtures of different polyisocyanates of the aforementioned kind.

Auxiliaries and additives present optionally in component d) are for example, surface-active substances, abrasive waxes, internal release agents, fillers, dyes, pigments, flame retardants, hydrolysis inhibitors, microbicides, flow assistants, antioxidants such as 2,6-di-tert-butyl-4-methylphenol, UV absorbers of the 2-hydroxyphenylbenzotriazole type or light stabilizers of the type of the HALS compounds unsubstituted or substituted on the nitrogen atom, such as Tinuvin® 292 and Tinuvin® 770 DF (Ciba Spezialitaten GmbH, Lampertheim, DE) or other commercially customary stabilizers, as described for example in "Lichtschutzmittel für Lacke" (A. Valet, Vincentz Verlag, Hanover, 1996) and "Stabilization of Polymeric Materials" (H. Zweifel, Springer Verlag, Berlin, 1997, Appendix 3, pp. 181-213), or any desired mixtures of these compounds.

Typically when preparing the coating compositions of the invention the individual components a), b) and optionally d) are mixed with one another. Subsequently component c, mixed optionally with further constituents of d), is added and the components are mixed.

Coating compositions based on the aqueous polyaspartic esters of the invention can be applied to any desired substrates in accordance with methods that are known per se, such as by spraying, spreading, flow coating or by means of rollers or doctor blades, for example. Examples of suitable substrates include metal, wood, glass, stone, ceramic materials, concrete, rigid and flexible plastics, textiles, leather or paper.

Curing can be performed at room temperature or at elevated temperature.

EXAMPLES

Unless noted otherwise, all percentages are by weight.

The pendulum hardnesses were determined by the method of König, DIN 53157.

The dynamic viscosities were determined at 23° C. using a rotational viscometer (ViscoTester® 550, Thermo Haake GmbH, D-76227 Karlsruhe).

The OH number was determined in accordance with DIN 53240 T.2.

Polyisocyanate 1

Bayhydur® 3100 (commercial product of Bayer MaterialScience AG, Leverkusen, DE), hydrophilic aliphatic polyisocyanate based on hexane 1,6-diisocyanate, having an NCO content of 17.4% by weight and a viscosity at 23° C. of 2800 mPa·s.

Polyisocyanate 2

Desmodur® N3400 (commercial product of Bayer MaterialScience AG, Leverkusen, DE), aliphatic polyisocyanate based on hexane 1,6-diisocyanate, having an NCO content of 21.8% by weight and a viscosity at 23° C. of 150 mPa·s.

Hydrophobic Polyaspartic Ester

Desmophen® NH1420 (commercial product of Bayer MaterialScience AG, Leverkusen, DE), polyaspartic ester based on 4,4'-diaminodicyclohexylmethane and diethyl maleate.

Preparation of the Hydrophilic Maleic Ester 432 g of dimethyl maleate, 493 g of triethylene glycol monomethyl ether and 0.9 g of dibutyltin oxide were weighed out into a three-necked flask with stirrer, distillation column and thermometer and the mixture was heated to 140° C. In parallel with the ensuing transesterification reaction the methanol liberated was distilled off under vacuum (30 mbar). After the theoretical amount of 96 g of methanol had distilled over, the reaction was terminated. The resulting product had an OH number of 0.

Preparation of the Hydrophilic Polyaspartic Ester 131 g of 4,4'-diaminodicyclohexylmethane were charged to a three-necked flask with stirrer, distillation column, thermometer and nitrogen blanketing and this initial charge was heated to 50° C. Subsequently 345 g of the above-prepared maleic ester were added dropwise at a rate such that the temperature did not exceed 50° C. When addition was at an end the temperature was raised to 60° C. and stirring was continued for 24 hours. The product had a viscosity at 23° C. of 1390 mPas.

Water could be added to prepare aqueous solutions of this polyaspartic ester. A 50% strength by weight solution in water had a viscosity at 23° C. of 25 mPa·s and an 80% strength by weight solution had a viscosity at 23° C. of 270 mPa·s.

Preparation of Coating Materials

The hydrophilic polyaspartic ester was dissolved in water in accordance with the table below and admixed with the stated amount of the polyisocyanate, with stirring. Subsequently this binder mixture was applied to a glass plate using a 180 µm drawdown frame and was cured at room temperature for 24 hours. In the case of the hydrophilic polyaspartic ester of the invention, clear, elastic films were obtained. Since the hydrophobic polyaspartic ester used by way of comparison was not soluble in water, it was not possible to obtain a homogeneous aqueous solution. Because of phase separation of the components, this resulted in films which were unusable.

TABLE 1

Composition and properties of the coating materials (amounts in parts by weight)

| | Example | | | | |
|---|---|---|---|---|---|
| | 1 | 2 | 3 | 4 | 4 |
| Hydrophilic polyaspartic ester | 80 | 80 | 50 | 80 | 80 |
| Hydrophobic polyaspartic ester | — | — | — | — | — |
| Water | 20 | 20 | 50 | 20 | 20 |
| Polyisocyanate 1 | 50 | 100 | 63 | 40 | 80 |
| Polyisocyanate 2 | — | — | — | — | — |

TABLE 1-continued

Composition and properties of the coating materials (amounts in parts by weight)

| | Example | | | | |
|---|---|---|---|---|---|
| | 1 | 2 | 3 | 4 | 4 |
| Appearance of film | clear | clear | clear | clear | clear |
| Pendulum hardness after 7 days | 14 s | 31 s | 21 s | 10 s | 13 s |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Hydrophilic polyaspartic esters of the general formula (I)

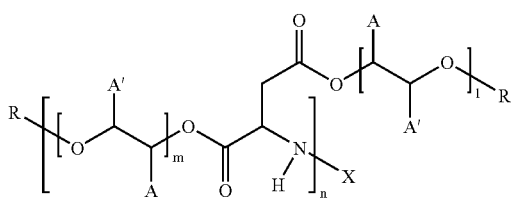

where
R is $C_1$-$C_4$ alkyl radical,
A and A' independently of one another are hydrogen or methyl,
X is an n-valent aliphatic, araliphatic or cycloaliphatic radical having 1 to 20 carbon atoms and optionally containing ether bridges,
l and m are natural numbers from 0 to 10 whose sum l+m=1 to 20, and
n is a natural number from 1 to 3.

2. Hydrophilic polyaspartic esters according to claim 1, wherein A and A' are hydrogen, X is an n-valent aliphatic or cycloaliphatic radical having 1 to 10 carbon atoms and optionally containing ether groups, and l and m independently of one another are 1, 2 or 3.

3. Hydrophilic polyaspartic esters according to claim 1 having number-average molecular weights of 300 to 1000 g/mol.

4. Hydrophilic polyaspartic esters according to claim 1, having viscosities at 23° C. of 50 to 5000 mPa·s.

5. Aqueous solutions or dispersions comprising hydrophilic polyaspartic esters according to claim 1.

6. Aqueous solutions or dispersions according to claim 5, wherein the polyaspartic ester contents are from 30% to 95% by weight.

7. Process for preparing hydrophilic polyaspartic esters comprising reacting maleic esters of the general formula (II)

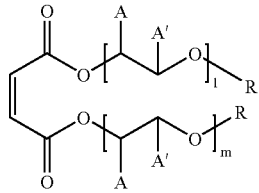

where
R is a $C_1$-$C_4$ alkyl radical,
A and A' independently of one another are hydrogen or methyl, and
l and m independently of one another are natural numbers from 0 to 10 and their sum l+m=1 to 20
with an n-valent amine of the formula (III)

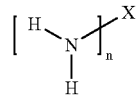

where
X is an n-valent aliphatic, araliphatic or cycloaliphatic radical having 1 to 20 carbon atoms and optionally containing ether bridges and
n is a natural number from 1 to 3
at temperatures of 0 to 100° C., preferably of 15 to 50° C.

8. A two-component coating composition comprising
a) at least one hydrophilic polyaspartic ester according to claim 1,
b water,
c) at least one polyisocyanate and
d) optionally auxiliaries and additives.

9. Coatings comprising polyaspartic esters according to claim 1.

10. Substrates coated with coatings according to claim 9.

11. The process of claim 7, wherein the process is carried out in the absence of solvent.

* * * * *